United States Patent
Robichaud et al.

(10) Patent No.: US 7,051,664 B2
(45) Date of Patent: May 30, 2006

(54) RETRIEVAL MECHANISM FOR AN UNDERWATER VEHICLE

(76) Inventors: Jason Robichaud, 265 Day St., Leominster, MA (US) 01453; James Giadone, 15 Olde Tavern Rd., Leominster, MA (US) 01453; Jose Flores, 21 Patricia Dr., Leominster, MA (US) 01453

( * ) Notice: Subject to any disclaimer, the term of this patent is extended or adjusted under 35 U.S.C. 154(b) by 112 days.

(21) Appl. No.: 10/794,944

(22) Filed: Mar. 5, 2004

(65) Prior Publication Data
US 2005/0204991 A1    Sep. 22, 2005

(51) Int. Cl.
*B63G 8/00* (2006.01)

(52) U.S. Cl. ........................................ 114/3.12; 37/338
(58) Field of Classification Search ................ 114/312; 37/313–316, 332, 338, 342, 307; 210/242.3
See application file for complete search history.

(56) References Cited

U.S. PATENT DOCUMENTS 8,731 A * 2/1852 Willey, Jr. .................... 37/338

OTHER PUBLICATIONS

Nadis, "Creatures of the Twilight Zone", *Popular Science*, Sep., 1998.

* cited by examiner

*Primary Examiner*—Jesus D. Sotelo
(74) *Attorney, Agent, or Firm*—Fish & Richardson P.C.

(57) ABSTRACT

An apparatus and related method of operation for collection of material by an underwater vehicle makes use of a number of arms extending outward from a body of the vehicle. The ends of the arms form an aperture for passing material into the body of the vehicle. One or more of the arms each includes a belt coupled to a drive mechanism for driving at least some portion of the belt generally toward the aperture. When driven, the belts form a current flowing into the vehicle propelling material for collection into the vehicle as well as mechanically force the material into the body. A spring-loaded mechanism can be used to force the arms together permitting retrieval of large object without jamming the retrieval mechanism.

12 Claims, 5 Drawing Sheets

RETRIEVAL MECHANISM FOR AN UNDERWATER VEHICLE

BACKGROUND

This invention relates to an underwater vehicle, and more particularly relates to a retrieving material using an underwater vehicle.

Numerous designs of underwater vehicles have been used over many decades for autonomous and remotely operated operations. For many tasks, material is to be retrieved or collected by the underwater vehicle. Various types of approaches have been used for retrieving of material. Perhaps the most common retrieval mechanism uses an articulated arm or arms, often using various forms of controllable grippers at the ends of the arms.

SUMMARY

In a general aspect, the invention features an apparatus and related method of operation for collection of material by an underwater vehicle. A number of arms extending outward from a body of the vehicle. The ends of the arms forming an aperture for passing material into the body of the vehicle. One or more of the arms each includes a belt coupled to a drive mechanism for driving at least some portion of the belt generally toward the aperture.

Aspects of the invention can include one or more of the following features.

All of the arms can include a belt coupled to a drive mechanism. Three or more arms can be used, with the ends of the arms forming the aperture into the main body. The arms can be arranged such that the far ends of the arms are more separated than the ends near the main body.

The arms can be arranged such that the near ends of the arms are movably attached to the body of the vehicle allowing the size of the aperture to be changed. A spring mechanism can be used to force the near ends of the arms towards one another.

A mechanism can be used for adjusting a separation of the far ends of the arms. This mechanism can include drive mechanism for controlling an angle between the arms.

Driving a belt on each of one or more of the arms forms a motion generally toward the aperture. This motion causes water current to flow generally toward the aperture. Material can be propelled into the aperture by the water current. Raised portions on the belts can mechanically couple the belts to the water such that the motions of the belts cause the water current to flow.

Aspects of the invention can have one or more of the following advantages.

The retrieval mechanism is simple with relatively few moving parts. This can result in inexpensive manufacturing and maintenance costs. This simplicity and low cost is particularly true as compared to articulated arms that can be both expensive and difficult to manipulate.

Remote control of the retrieval process is tolerant to relative inaccuracy of in the positioning of the arms. A wide aperture at the far end of the arms captures material in a relatively large area making it easier for the operator to maneuver the vehicle into a suitable position for collecting material located using an on-board camera.

Other features and advantages of the invention are apparent from the following description, and from the claims.

DESCRIPTION OF DRAWINGS

FIG. 4A is a top schematic view of a spring-loaded retrieval mechanism; FIG. 4B is a perspective view of the spring-loaded mechanism; and FIG. 4C is a front view.

DETAILED DESCRIPTION

Figure 1:
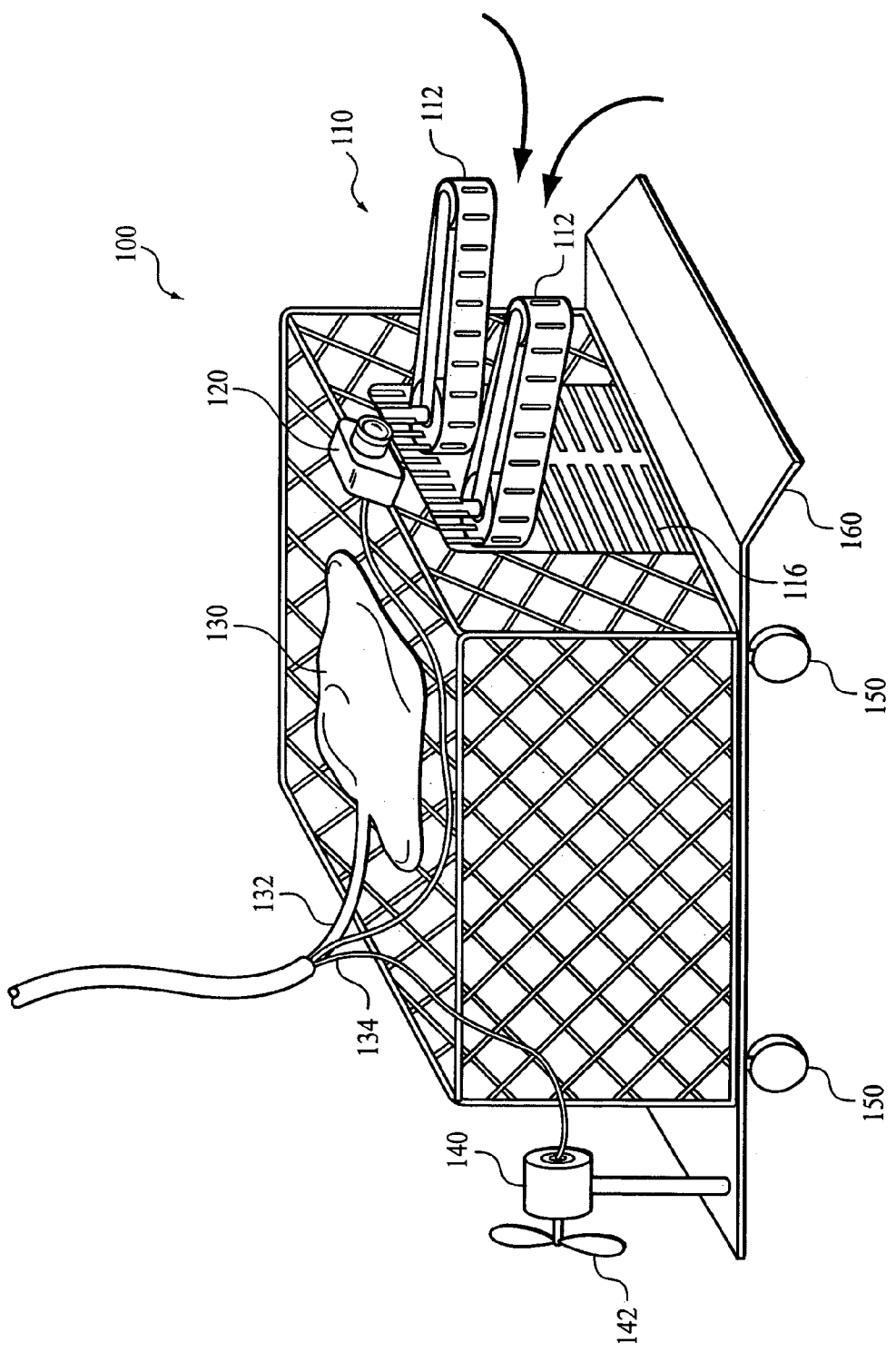
FIG. 1 is a perspective view of an underwater vehicle.

Referring to FIG. 1, an underwater vehicle 100 includes a retrieval mechanism 110 for collecting material into the main body of the vehicle. For example, the vehicle can be used to collect underwater plants for biological research. The retrieval mechanism 110 includes arms 112 extending outward from the main body. The ends of the arms nearest the main body form an aperture through which material is passed into and collected in the main body. The arms have flexible conveyor belts along their outside surface which are driven by motors to collect the material. Driving the belts forms motion on the inner surfaces of the arms toward the aperture. Material to be collected is forced toward the aperture as a result of water current formed by the motion of the belts and/or through mechanical coupling of the material to the belts, for example, by friction or by being caught raised portions of the outside surface of the belt.

The underwater vehicle 100 includes components that allow the vehicle to be remotely controlled and positioned underwater. An air bladder 130 is used to adjust the buoyancy of the vehicle, allowing the vehicle to rise and fall through the water. Motors 140 drive propellers 142 that are used to drive the vehicle forward and backward and to steer the vehicle using differential driving of the motors 140. The vehicle also has wheels 150 attached to the bottom of the main body that permit the vehicle to roll on the bottom of a body of water for collecting material on or near the bottom. To aid in collecting material along the bottom, a ramp 160 extends from the bottom of the vehicle to approximately the level of the bottom when then vehicle is supported by its wheels. This ramp keeps bottom material from passing under the vehicle when the vehicle is propelled forward. This vehicle is controlled by an operator from the surface using an "umbilical" cord that includes an air hose 132 for adjusting the amount of air in the bladder 130 and includes electrical cables that include cables for powering the various motors on the vehicle. The underwater vehicle also includes a camera 120 and associated lights that provide a view of the outward ends of the arms 112. A camera signal is sent from the camera through the umbilical cord to the surface, where an operator can view the image and control the vehicle according to the image.

The main body of the vehicle uses mesh walls that allow water to pass through the main body while capturing the material collected using the arms. That is, water forced into the main body by the retrieval mechanism can exit the vehicle through the walls. The aperture formed by the arms is part of an opening in the main body. The opening includes a portion that extends beyond the aperture to allow relatively larger material to pass into the vehicle. In order that material does not inadvertently leave the vehicle, a "baleen" portion 116 is formed using flexible strips. The strips can be deflected by material being forced into the body by the arms, but are rigid enough to keep the material from leaving the vehicle, even if the belts are not driven. In this version of the vehicle, the baleen portion is formed using nylon cable ties that are secured along the edge of the opening to the main body and meet at the middle of the opening. The baleen and the main body with its mesh sides has some characteristics that are similar to a lobster trap that allows lobsters to enter but not to easily leave the trap.

Figure 2:
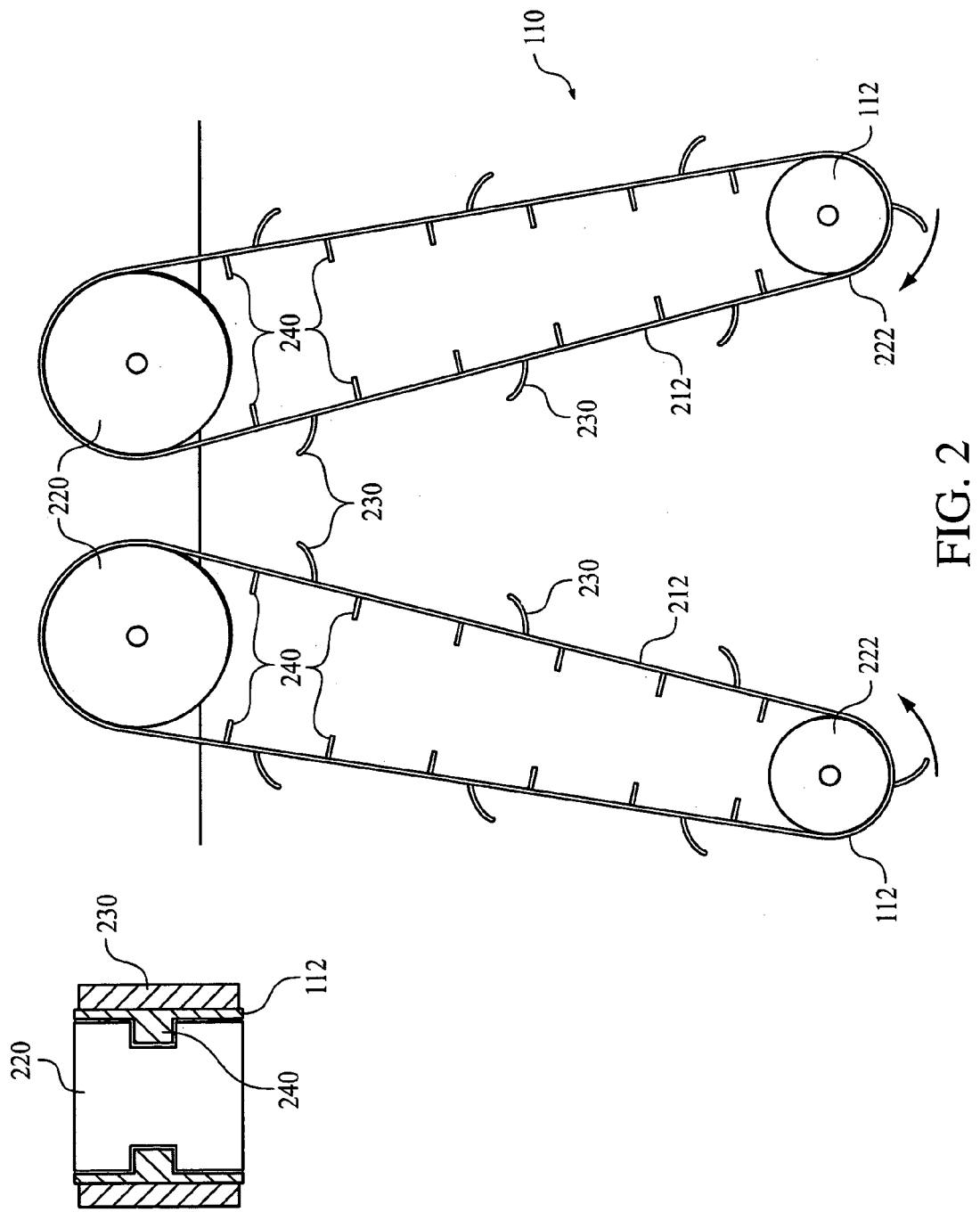
FIG. 2 is a cross-sectional view of the arms of the retrieval mechanism of the vehicle.

Referring to FIG. 2, the arms 112 of the retrieval mechanism 110 includes two arms 112. The arms are angled outward so that the ends of the arms farthest away from the main body form a larger aperture than the ends nearest to the main body. Each arm 112 has a flexible conveyor belt 212 on its exterior surface. Each belt is made of rubber, and is similar to a caterpillar track used in toy vehicles. Each belt is approximately two inches wide. The belt is held by two pulleys 220 and 222, one at each end of the arm. In this version of the retrieval mechanism, the pulley 222 at the end away from the main body has a smaller diameter than the pulley 220 near the main body. Each pulley has a grove around the circumference approximately half way along the width of the belt. The belt has tabs 240 that fit in the grove. These tabs aid in keeping the belt aligned on the pulleys rather than shifting in the direction of the axis of the pulleys. The pulleys 220 near the main body are driven by motors (not shown in FIG. 2) causing the belt 212 to move. The pulleys 222 are free to turn allowing the belt to rotate such that the inner portions of the belts move toward the aperture. The outer surface of the belts 212 include "cilia" 230, which are protrusions or ridges that help move material toward the aperture and into the main body and that increase the magnitude of the water current. In this version of the belts, the cilia are formed of pliable material and are generally curved in the direction of travel of the belts.

Figure 3B:
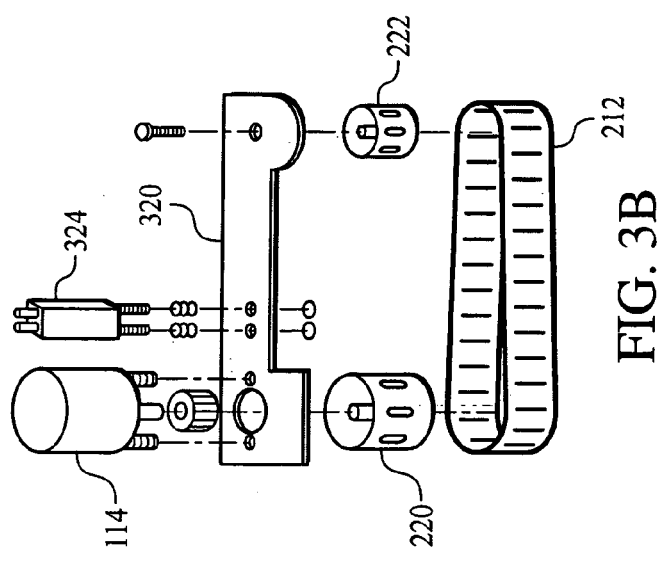
FIG. 3B is an exploded view of the arm.
Figure 3A:
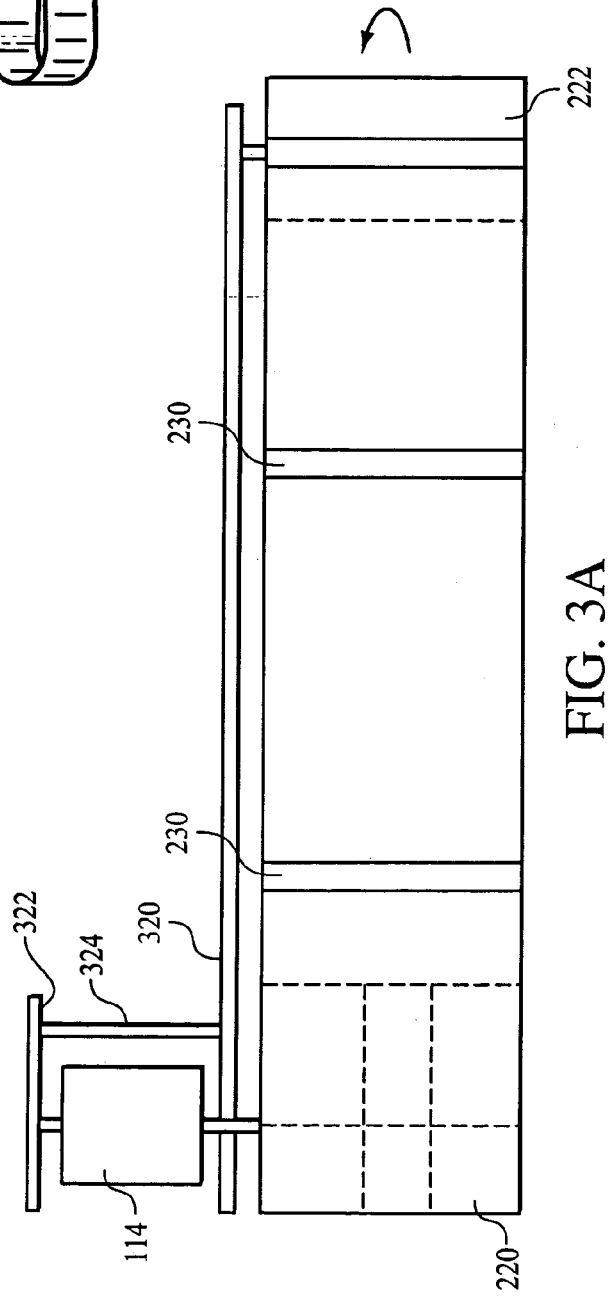
FIG. 3A is a side view of an arm of the retrieval mechanism.

Referring to FIGS. 3A–B, each arms 112 includes a motor 114 that drives the belt 212. The motor is directly coupled to the pulley 220 at the near end of the arm. A rigid frame is made up of a plate 322 that attaches to the main body of the vehicle, an elongated part 320 that holds the pulleys at a fixed distance from one another and on rotational axes perpendicular to the part 320, and a vertical part 324 that couples the plate 322 and the elongated part 320.

In one version of the retrieval mechanism, the speed of the motors is fixed (i.e., the operator has an on-off control of the motor). The motor speed is relatively fast as compared to the speed at which material is propelled into vehicle. In this version, the primary mode of propulsion of the material is through the current induced by the moving belts. Alternatively, the motors move more slowly, for example, if the primary move of propulsion of material is by direct physical contact with the belts (or the cilia on the belts) rather than indirectly due to a current formed by the belt motion. Also, if the material if fragile, for example like a jelly, a slower speed may be chosen to not disturb the material as it is propelled by the retrieval mechanism either by current or physical contact. A variable-speed motor can also be used. Such a motor can be controlled from the surface by the operator, for example, according to the material being retrieved. The motor is optionally reversible, thereby allowing expulsion of material that becomes stuck in the retrieval mechanism, for example, because it is too large for the aperture into the main body.

Figure 4A:
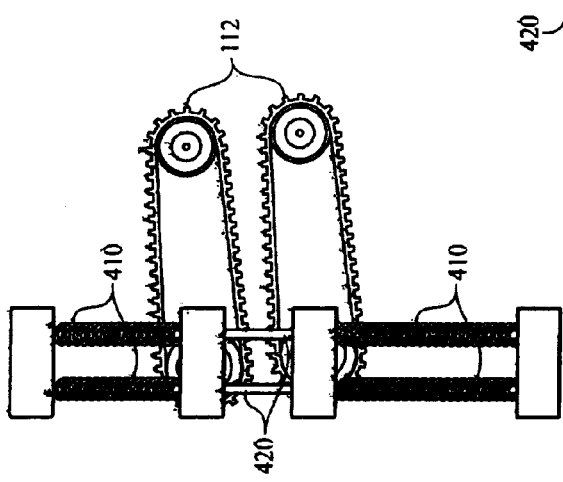
FIGS. 4A–4C are views of a spring-loaded retrieval mechanism.
Figure 4B:
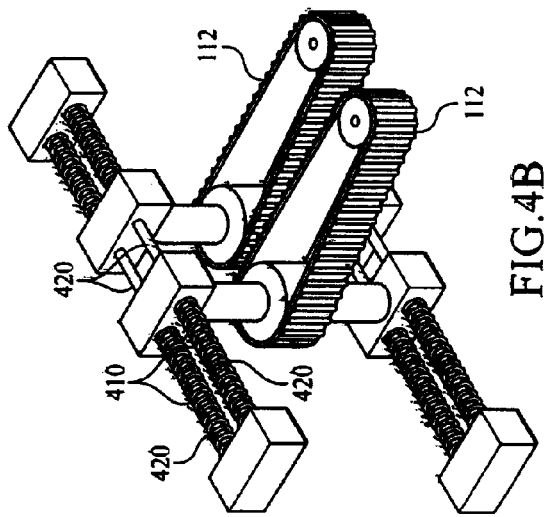
Figure 4C:
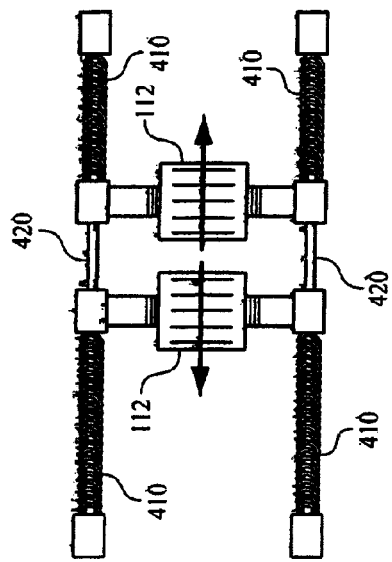

Referring to FIGS. 4A–C, in an alternative arrangement of the retrieval mechanism, the arms are coupled to the main body such that they can slide such that the aperture formed by the near ends of the arms can widen and narrow. Springs 410 force the arms to slide together along guide rods 420 while maintaining the angle between the arms. The drive motors are attached to the arms and slide along with the arms, thereby not requiring a drive mechanism that needs to adapt to the opening size. If a large object is captured by the arms, the arms are forced apart as the object is passed through the aperture into the main body. This arrangement permits retrieval of relatively small objects while allowing large objects to pass through the mechanism without jamming.

Figure 5A:
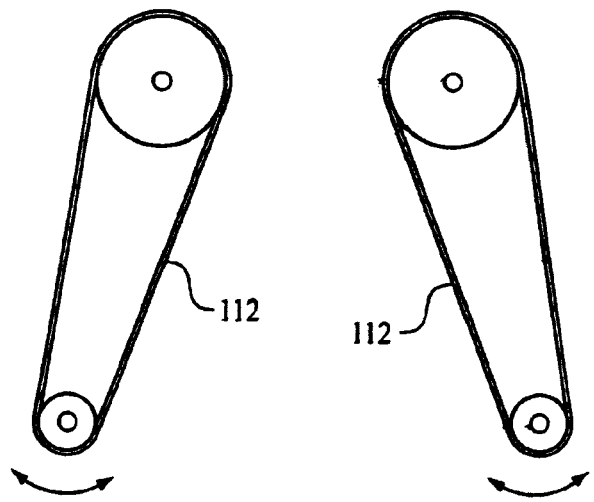
FIGS. 5A–B are schematic views of alternative arrangements of arms of a retrieval mechanism.
Figure 5B:
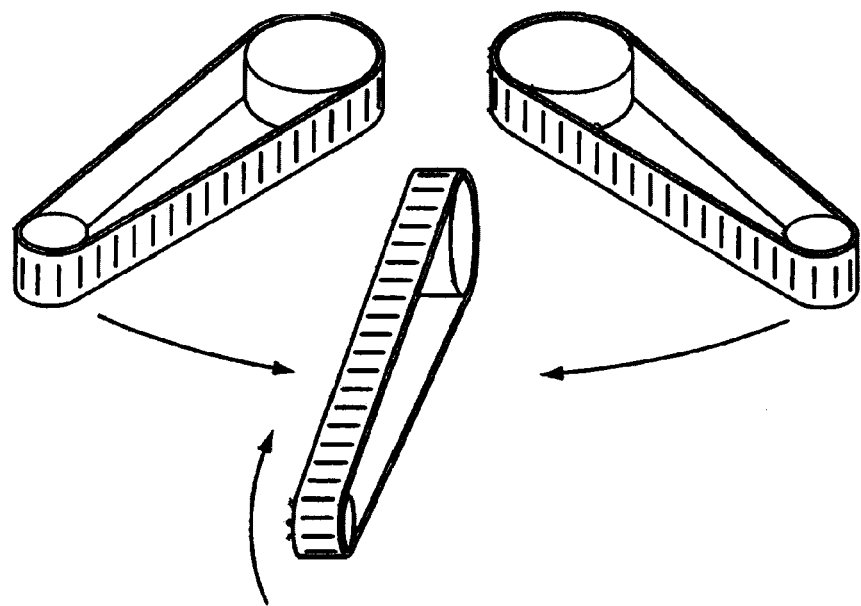

Referring to FIG. 5A, in another alternative arrangement of the retrieval mechanism, that arms can pivot around the axis of the pulleys at the near ends of the arms. The pivoting is controlled by a separate drive motor. The pivoting allows the far ends of the arms to be brought together to capture material by direct contact or by increasing the rate of water flow resulting from the reduced separation of the moving belts. Referring to FIG. 5B, other alternative arrangements of the retrieval mechanism use more than two arms. In FIG. 5B, three arms each with belts are shown forming a generally triangular aperture into the main body. Features of the various embodiments can be combined. For example, the spring arrangement or the controlled pivoting arrangement can be combined with more than two arms. Furthermore, it is not necessary that all the arms have driven belts. For example, an arm with a driven belt may be opposed by one or more arms that do not have belts, but that serve to guide the material when it is propelled toward the main body.

Alternative belt surfaces can be used in various of the arrangements discussed above. Rather than cilia or other ridge-like protrusions, the belts can have raised "spikes" or other types of raised portions that can engage the material being retrieved and/or aid in creating the inbound water current. The cilia can also overlap or interlock as the belts get closer together nearer to the body, thereby trapping material as it is retrieved.

In the version of the underwater vehicle described above, the main body of the vehicle is approximately 24 inches long and the arms are approximately 12 inches long. Larger or smaller version of the arms and narrower or wider belts can be used depending on the application.

The retrieval mechanism is not necessarily used with a vehicle. The near end of the arms can be fixed, for example to capture material for a fixed underwater body. The retrieval mechanism can be used on the surface of the water rather than underwater. Large versions of the arms can be used to applications such as retrieval of logs from the surface or underwater in a river.

It is to be understood that the foregoing description is intended to illustrate and not to limit the scope of the invention, which is defined by the scope of the appended claims. Other embodiments are within the scope of the following claims.

What is claimed is:

1. An apparatus for retrieving material using an underwater vehicle, the apparatus comprising:
   a plurality of arms extending outward from a body of the vehicle, each arm having a distal end and a proximal end, the proximal ends of the arms forming an aperture for passing material into the body of the vehicle; and
   wherein at least one of the arms each includes a belt coupled to a drive mechanism for driving at least some portion of the belt generally toward the aperture.

2. The apparatus of claim 1 wherein each of the arms includes a belt coupled to a drive mechanism.

3. The apparatus of claim 2 wherein the apparatus includes at least three or more arms whose proximal ends form the aperture.

4. The apparatus of claim 1 wherein the arms are arranged such that the distal ends of the arms are more separated than the proximal ends.

5. The apparatus of claim 1 wherein the arms are arranged such that the proximal ends of the arms are movably attached to the body of the vehicle allowing the size of the aperture to be changed.

6. The apparatus of claim 5 wherein the apparatus includes a spring mechanism forcing the proximal ends of the arms towards one another.

7. The apparatus of claim 1 wherein the apparatus includes a mechanism for adjusting a separation of the distal ends of the arms.

8. The apparatus of claim 7 wherein the mechanism for adjusting the separation includes a drive mechanism for controlling an angle between the arms.

9. The apparatus of claim 1 wherein the drive mechanism includes a motor coupled to at least one of the belts.

10. A method for retrieving material underwater, comprising:

providing a plurality of arms expending outward from a body of the vehicle, each arm having a distal end and a proximal end, the proximal ends of the arms forming an aperture for passing material into the body of the vehicle; and driving a belt on each of at least one of the arms such that at least some portion of the belt forms a motion generally toward the aperture.

11. The method of claim 10 wherein driving the belts includes forming a water current flowing generally toward the aperture.

12. The method of claim 11 wherein each belt includes a plurality of raised portions mechanically coupling the belts to the water such that the motion of the belts cause the water current to flow.

* * * * *